United States Patent [19]

Chou

[11] Patent Number: 4,837,332
[45] Date of Patent: Jun. 6, 1989

[54] PROCESS FOR BLOCKING AMINO ACIDS WITH THE TERTIARY-ALKOXYCARBONYL GROUP

[75] Inventor: Chih-Yueh Chou, Elk Grove Village, Ill.

[73] Assignee: PPG Industries, Inc., Pittsburgh, Pa.

[21] Appl. No.: 837,228

[22] Filed: Mar. 7, 1986

[51] Int. Cl.$^4$ .......................................... C07D 233/84
[52] U.S. Cl. .................................... 548/321; 548/344;
548/497; 548/533; 562/443; 562/445; 562/446;
562/556; 562/557; 562/560; 562/561; 562/567;
562/571; 562/575
[58] Field of Search ............... 548/344, 321, 497, 533;
562/341, 443, 575, 445, 446, 556, 557, 560, 561,
567, 571

[56] References Cited

FOREIGN PATENT DOCUMENTS 2315120 10/1973 Fed. Rep. of Germany ...... 548/344

OTHER PUBLICATIONS

Wertheim, E., *Textbook of Organic Chemistry*, 3rd ed., McGraw Hill, New York, 1951, pp. 280–282, 795 and 796.
*Webster's Seventh New Collegiate Dictionary*, G and C Merriam Co., Springfield, MA, 1965, p. 669.
U. Ragnarsson et al., *Acta Chemica Scandinavica*, vol. 26, No. 6, pp. 2550–2551 (1972).
M. Fridkin et al., *Canadian Journal of Chemistry*, vol. 49, pp. 1578–1581 (1971).
Klee and Brenner, "t-Butylcarbonyl—imidazol und t-Butyloxycarbonyl-hydrazin", *Helvetica Chemica Acta*, vol. 44, No. 7 (1961), pp. 2151–2153 with translation.
Ali, Fahrenholz and Weinstein, "Simple Method for the Synthesis of Some Boc–Amino Acids", *Angew. Chem. Internat. Edit.*, vol. 11, No. 4, (1972), p. 289.
Guibe-Jampel, Bram, and Vilkas, "Derives 'Acyles' du N-Methyl Imidazole", *Bull. Soc. Chim. Fr.*, No. 3 (1973), pp. 1021–1026 with translation.
Bram, "Synthesis de N-tert-Butyloxycarbonyl Aminoacides", *Tetrahedron Letters*, No. 6 (1973) pp. 469–472 with translation.
Ragnarsson et al., "Tert-Butyloxycarbonyl-L-Proline", *Organic Syntheses*, vol. 53 (1973), pp. 25–29.
Guibe-Jampel, Bram, Wakselman, and Vilkas, "Water-Soluble Reagents for the Tert-Butoxycarbonylation of Amines", *Synthetic Communications*, vol. 3, No. 2 (1973), pp. 111–114 with translation.

*Primary Examiner*—Richard A. Schwartz
*Attorney, Agent, or Firm*—George D. Morris

[57] ABSTRACT

Amino acid salt having at least one unblocked amino group and comprising at least one cation which has a nitrogen cationic atom is reacted with 1-(tertiary-alkoxycarbonyl)imidazole in the liquid phase and in the presence of essentially inert organic solvent having a dielectric constant at 25° C. of at least about 4, to produce N-(tertiary-alkoxycarbonyl)-blocked amino acid salt.

24 Claims, No Drawings

PROCESS FOR BLOCKING AMINO ACIDS WITH THE TERTIARY-ALKOXYCARBONYL GROUP

BACKGROUND OF THE INVENTION

Amino acids are often employed as raw materials in the preparation, by a sequence of reactions, of compounds having various uses. In many of these sequences as for example peptide synthesis, it is necessary to reversibly block an amino or imino group of a salt of the amino acid in order that the blocked compound may undergo further reactions which would otherwise irrevocably destroy the amino or imino group, and yet permit later regeneration of the amino or imino group.

The benzyloxycarbonyl group (also known as the carbobenzoxy group or the (phenylmethoxy)carbonyl group) has been extensively used for this purpose. The benzyloxycarbonyl group may be introduced by reacting a salt of the amino acid with a benzyl haloformate such a benzyl chloroformate or benzyl bromoformate. The blocked amino acid salt may then be reacted to form reaction products in which the amino or imino group remains blocked. In most cases, it is eventually desired to remove the benzyloxycarbonyl group and regenerate the amino or imino group. However, the benzyloxycarbonyl group is not easily removed under mild conditions. Consequently, hydrogenation is customarily used for this purpose. Hydrogenation is not a desirable reaction to carry out since it employs hydrogen which is extremely flammable and since it usually employs a catalyst such as palladium on carbon or Raney nickel. A further disadvantage of the hydrogenation process is that toluene is left in the reaction mixture as a contaminant.

Use of the tertiary-butoxycarbonyl group (also known as the 1,1-dimethylethoxycarbonyl group) possesses several advantages over use of the benzyloxycarbonyl group as the blocking group. One such advantage is that the tertiary-butoxycarbonyl group may be removed and the amino or imino group regenerated by treatment with strong acid to a pH of about 1 or less under mild temperature conditions. Another advantage is that the by-products of the tertiary-butoxycarbonyl group upon removal are isobutene (viz., 2-methylpropene) and carbon dioxide, which are both gasses and therefore easily removed from the reaction mixture. The principal disadvantages center on introduction of the tertiary-butoxycarbonyl group. Di-tertiary-butyl dicarbonate,

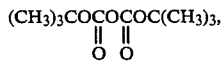

has been used for this purpose, but the compound is very expensive and contributes only one tertiary-butoxycarbonyl group for blocking purposes; and remaining portion of the molecule reacts to form carbon dioxide and either tertiary-butanol or isobutene. Another group of compounds, the unsubstituted or ring-substituted tertiary-butyl phenyl carbonates, have also been employed but a byproduct of the reaction is the corresponding phenol which is difficult to remove from the reaction mixture. Yet other compounds that have been employed include tertiary-butoxycarbonylazide, tertiary-butoxycarbonylfluoride, 1-tertiary-butoxycarbonyl-1,2,4-triazole, and 1-tertiary-butoxycarbonyl-3-methylimidazolium salts.

Klee and Brenner, *Helvetica Chimica Acta*, volume 44, pages 2151–2153, disclosed reacting sodium glycinate and 1-(tertiary-butoxycarbonyl)imidazole in a sealed tube for 15 hours at 110° C. to produce, after acidification, N-(tertiary-butoxycarbonyl)glycine in 46 percent yield. Similarly, N-(tertiary-butoxycarbonyl)-DL-phenylalanine was obtained in 25 percent yield. These yields are low and the conditions unsuitable for commercially viable processes. Indeed, Bram, *Tetrahedron Letters* No. 6, pages 469–472, indicates that 1-(tertiary-butoxycarbonyl)imidazole is stable but only slightly reactive with respect to the amine compounds.

The Invention

A process has been discovered which uses 1-(tertiary-butoxycarbonyl)imidazole or 1-(tertiary-amyloxycarbonyl)imidazole as the blocking agent for organic salts of amino acids and which produces the desired product in high yields under conditions which are commercially viable. Accordingly, in a process wherein precursory amino acid salt comprising an amino acid anion having at least one unblocked amino or imino group and comprising at least one cation is reacted with 1-(tertiary-alkoxycarbonyl)imidazole to produce N-(tertiary-alkoxycarbonyl)-blocked amino acid salt in which the tertiary-alkoxycarbonyl group is tertiary-butoxycarbonyl or tertiary-amyloxycarbonyl, one embodiment of the invention is the improvement wherein the cation contains a nitrogen cationic atom and the reaction is conducted in the liquid phase and in the presence of essentially inert organic solvent having a dielectric constant at 25° C. of at least about 4.

Another embodiment of the invention is a process comprising (a) reacting amino acid having at least one unblocked amino or imino group, which amino acid is dissolved or suspended in essentially inert organic solvent having a dielectric constant at 25° C. of at least about 4, with nitrogenous base to form a solution or suspension of precursory amino acid salt comprising an amino acid anion having at least one unblocked amino or imino group and further comprising at least one cation containing a nitrogen cationic atom; and (b) reacting, in the liquid phase and in the presence of essentially inert organic solvent having a dielectric constant of at least about 4, at least a portion of the precursory amino acid salt and 1-(tertiary-alkoxycarbonyl)imidazole to produce N-(tertiary-alkoxycarbonyl)-blocked amino acid salt, wherein the tertiary-alkoxycarbonyl group is tertiary-butoxycarbonyl or amyloxycarbonyl.

The tertiary-amyloxycarbonyl group functions similarly to the tertiary-butoxycarbonyl group as a blocking group and it possesses analogous advantages over the benzyloxycarbonyl group. The gaseous byproducts of removal of the tertiary-amyloxycarbonyl group are 2-methyl-2-butene and carbon dioxide.

Amino acids, the nitrogenous salts of which are used as reactants in the blocking reaction may be widely varied. They may be polypeptides of two, three, four, five, or more fundamental amino acid units. More usually, however, they are the fundamental amino acids themselves. Examples include glycine, alanine, valine, norleucine, leucine, isoleucine, serine, threonine, cysteine, cystine, methionine, arginine, nitroarginine, lysine, ε-(benzyloxycarbonyl)lysine, ornithine, aspartic acid, β-benzylaspartic acid, glutamic acid, hydroxyglutamic acid, phenylalanine, tyrosine, iodogorgoic acid, thyroxine, tryptophan, proline, hydroxyproline, histidine, canavanine, canaline, citrulline, djenkolic acid, dihydroxyphenylalanine, and 2-thiolhistidine. The amino acids may individually have the L-configuration or the D-configuration, although the L-configuration is more common. Mixtures of amino acids, including racemic mixtures, may also be used.

The precursory amino acid salt used as a reactant in the first embodiment of the invention may be from any source. More usually, however, the salt is prepared in situ in accordance with the first step of the second embodiment.

The nitrogenous base which can be reacted with the amino acid to form the amino acid salt can be widely varied. Ammonia can be used, but it is preferred that the base be such that the nitrogen cationic atom of the cation of the precursory amino acid salt be directly bonded to at least one carbon atom. Examples of classes of nitrogenous bases that can be used include primary amines, secondary amines, tertiary amines, quaternary ammonium hydroxides, amidines, guanidines, and the pyridines. These are only illustrative and there are numerous other classes of nitrogenous bases that can be used. The essential characteristic of the nitrogenous base employed is that the resulting precursory amino acid salt can be solubilized in the essentially inert organic solvent at least to the degree that a liquid phase blocking reaction can occur. Preferably the nature of the precursory amino acid salt and the relative proportions of the essentially inert organic solvent and the precursory amino acid salt are such that the precursory amino acid salt is essentially completely dissolved.

Examples of nitrogenous bases that can be used include triethylamine, diisopropylethylamine, tetramethylammonium hydroxide, tetramethylammonium methoxide, benzyltrimethyl ammonium hydroxide, tetraethylammonium hydroxide, 1,5-diazabicyclo[4.3.0]non-5-ene (DBN), 1,8-diazabicyclo[5.4.0]undec-7-ene (DBU), 13H-dibenzo[a,i]carbazole, and 1,1,3,3-tetramethylguanidine (TMG). One nitrogenous base or a plurality of nitrogenous bases may be used as desired.

Ordinarily the nitrogenous base has a pKa in water of greater than 7. In many cases, the pKa in water is at least about 8. It is preferred that the nitrogenous base have a pKa in water of at least about 10.

The essentially inert organic solvent is a liquid at the temperature of the blocking reaction and serves to dissolve the precursory amino acid salt and the 1-(tertiary-alkoxycarbonyl)imidazole in order for the blocking reaction to occur in the liquid phase. This solvent consists essentially of one or more organic solvent compounds which do not react with 1-(tertiary-alkoxycarbonyl)imidazole. If any organic solvent species which do react with 1-(tertiary-alkoxycarbonyl)imidazole are present, they are present in very small quantities relative to the nonreactive organic solvent species. In most cases the essentially inert organic solvent contains less than about 5 parts of reactive organic solvent species per thousand parts of the essentially inert organic solvent, by weight. It is preferred that no reactive organic solvent species be present.

The essentially inert organic solvent, which is polar aprotic solvent, has a dielectric constant at 25° C. of at least about 4. Usually the dielectric constant at 25° C. is at least about 10. Often the dielectric constant at 25° C. is at least about 25. It is preferred that the essentially inert solvent have a dielectric constant at 25° C. of at least about 35.

Examples of suitable essentially inert organic solvent compounds which can be used include dimethyl sulfoxide (DMSO), acetonitrile, N,N-dimethylformamide (DMF), tetrahydrofuran (THF), methylene chloride, chloroform, nitrobenzene, chlorobenzene, ortho-dichlorobenzene, meta-dichlorobenzene, p-chlorotoluene, 1,1,2,2-tetramethylurea, sulfolane, ethyl acetate, 4-methyl-2-pentanone, benzonitrile, propionitrile, N-methylpropionamide, N-methylpyrrolidone (NMP), ethyl cyanoacetate, acetone, nitromethane, butyronitrile, isobutyronitrile, 2-butanone, ethyl formate, methyl acetate, nitroethane, 1-chloropropane, 2-chloropropane, valeronitrile, 3-pentanone, N,N-dimethylacetamide, methyl propionate, propyl formate, valeronitrile, 1-nitropropane, 2-nitropropane, 1-chlorobutane, 2-chlorobutane, 1-chloro-2-methylpropane, 2-chloro-2-methylpropane, capronitrile, 4-methylvaleronitrile, cyclohexanone, 1,1-dichloroethane, 1,2-dichloroethane, methyl cyanoacetate, ethyl propionate, isobutyl formate, methyl butyrate, ethyl cyanoacetate, butyl acetate, ethyl butyrate, isobutyl acetate, toluic nitrile, 2-methoxyethyl acetate, capronitrile, ethyl acetoacetate, 1,1,1-trichloroethane, and ethylene diacetate. Only one essentially inert organic solvent compound or a mixture of such compounds may be used as desired.

In the preferred embodiment where the salt-forming reaction is conducted in an essentially inert organic solvent system, the amount of essentially inert organic solvent present is sufficient to dissolve at least a portion of the precursory amino acid salt produced. Preferably the amount of such solvent present is sufficient to dissolve all of the precursory amino acid salt produced. The maximum amount of essentially inert organic solvent used is not governed by theory, but by practical considerations such as the quantities of liquid that must be handled and whether or not the precursory amino acid salt is to be recovered prior to reaction with the blocking agent or reacted in situ with the blocking agent. Usually the weight ratio of the essentially inert organic solvent to the amino acid having at least one unblocked amino or imino group initially present in the sale-forming reaction is at least about 3:1. In many cases the weight ratio is in the range of from about 3:1 to about 25:1. Preferably the weight ratio is in the range of from about 5:1 to about 20:1.

Similarly, the amount of essentially inert organic solvent present during the blocking reaction may also vary widely. In general, sufficient essentially inert organic solvent should be present so that the blocking reaction may be conducted in the liquid phase. Although it is necessary only that a portion of the precursory amino acid salt be initially dissolved in the essentially inert organic solvent, it is preferred that all of the precursory amino acid salt be dissolved prior to beginning the blocking reaction. The maximum amount of essentially inert organic solvent that can be present is not governed by theory, but by practical considerations such as the quantities of liquid that must be handled and the ease with which the product may be recovered. Ordinarily the weight ratio of essentially inert organic solvent to the precursory amino acid salt initially present is at least about 1:1. Often the weight ratio is in the range of from about 1:1 to about 20:1. Preferably the weight ratio is in the range of from about 2:1 to about 10:1.

The 1-(tertiary-alkoxycarbonyl)imidazole is usually unsubstituted, but one or more minor substituents may be present provided they do not preclude the blocking reaction. If substitution is present, it is usually on the imidazolic portion of the molecule.

There are many advantages in using 1-(tertiary-alkoxycarbonyl)imidazole as the blocking agent in accordance with the invention. One such advantage is that the 1-(tertiary-alkoxycarbonyl)imidazole is easily prepared by reacting the appropriate 1,1'-carbonylbis(1H-imidazole) with tertiary-butyl alcohol or tertiary-amyl alcohol in the presence of a solvent such as normal hexane. See the Klee and Brenner paper earlier cited. Another advantage is that after the amino acid salt has been blocked, the by-product imidazole resulting from the blocking reaction is easily removed from the reaction mixture by washing with water. A further advantage is that the pKa of imidazole is close to 7; therefore its presence does not significantly change the pH of the reaction system.

1-(Tertiary-alkoxycarbonyl)imidazole will react with water under the proper conditions to form imidazole, carbon dioxide, and tertiary-alkyl alcohol. To the extent that this reaction does occur, it represents a loss of the blocking agent. The amount of water or other proton doner should therefore be maintained reasonably low.

While in the preferred embodiment the reaction mixture during the blocking reaction is essentially anhydrous, nevertheless in some situations it is desirable to tolerate a small amount of water in the system. Such a situation can occur where a quaternary ammonium hydroxide is reacted with amino acid in accordance with the first step of the second embodiment of the invention to form the precursory amino acid salt and water as a by-product. Inasmuch as the amount of essentially inert solvent is large compared to the amount of water produced, it may be more advantageous to forego drying the reaction mixture before proceeding to the second step and to accept the resulting loss of 1-(alkoxycarbonyl)imidazole. Of course such losses can be reduced or even eliminated by drying the first reaction mixture when desired. A more preferable way to avoid such losses is to employ a nitrogenous base which does not give rise to the formation of water during the salt-forming reaction. Nitrogenous bases such as tertiary amines, DBN, DBU, and 1,1,3,3-tetramethylguanidine are therefore most often used. Another situation in which a small amount of water can be tolerated is where a small amount of water is introduced to the system of the salt-forming reaction or to the system of the blocking reaction with one or more of the reactants and/or the solvent, and where drying is not warranted in view of the small amount of water present.

The salt-forming reaction can proceed satisfactorily even in an aqueous medium. The maintenance of low amounts of water assumes direct importance in the medium of the blocking reaction. Consequently, if steps are taken to separate all but small amounts of water from the precursory amino acid salt prior to its introduction to the medium of the blocking reaction, the amount of water present in the salt-forming reaction is relatively unimportant. However in the preferred embodiment, the salt is first formed in an essentially inert organic solvent system of low water content and then at least a portion of the precursory amino acid salt is reacted in situ with 1-(tertiary-alkoxycarbonyl)imidazole to produce N-(tertiary-alkoxycarbonyl)-blocked amino acid salt. In this embodiment the water content of the salt-forming reaction medium is important inasmuch as the water present is carried over into the blocking reaction medium.

It is accordingly preferred that the water content of the reaction mixture during precursory amino acid salt formation be less than about 1 percent by weight. In many cases the water content is less than about 0.5 percent by weight. Typically the water content is less than about 0.1 percent by weight. It is preferred that the salt-forming reaction be conducted under substantially anhydrous conditions.

The water content of the reaction mixture during the blocking reaction should be less than about 1 percent by weight. Often the water content is less than about 0.5 percent by weight. Ordinarily the water content is less than about 0.1 percent by weight. It is preferred that the blocking reaction be conducted under substantially anhydrous conditions.

The equivalent ratio of the nitrogenous base to the amino acid introduced to the salt-forming reaction may be widely varied, but typically it is in the range of from about 0.9:1 to about 5:1. Often the equivalent ratio is in the range of from about 1:1 to about 3:1. An equivalent ratio in the range of from about 1.5:1 to about 2.5:1 is preferred.

Then the nitrogenous base is one that would significantly react with 1-(tertiary-alkoxycarbonyl)imidazole, it should be used in about stoichiometric proportions with the amino acid or the excess should be substantially removed prior to the blocking reaction. If the nitrogenous base is not significantly reactive with 1-(tertiary-alkoxycarbonyl)imidazole as is preferred, the excess, if any, may be retained in the system.

The equivalent ratio of the 1-(tertiary-alkoxycarbonyl)imidazole to the precursory amino acid salt introduced to the blocking reaction is similarly susceptible to wide variation. Ordinarily the equivalent ratio is in the range of from about 0.9:1 to about 3:1. Often the equivalent ratio is in the range of from about 1:1 to about 2:1. An equivalent ratio in the range of from about 1.1:1 to about 1.7:1 is preferred.

The temperature at which the reactions are conducted may vary considerably, but ordinarily they are in the range of from about the freezing point of the system to about 45° C. Typically the temperatures are in the range of from about −10° C. to about 35° C. Temperatures in the range of from about 10° C. to about 30° C. are preferred.

The pressures at which the reactions are conducted may also be widely varied. Atmospheric and slightly superatmospheric pressures are generally employed, although greater or lesser pressures may be used.

The reactions may be carried out batchwise, continuously, semibatchwise or semicontinuously.

The blocked amino acid salt may be recovered from the reaction mixture in which it was formed by any of the various techniques known to the art. Water washing, extraction, precipitation, stripping, and drying are examples of some of the techniques which can be used.

The invention is further described in conjunction with the following examples which are to be considered illustrative rather than limiting, and in which all parts are parts by weight and all percentages are percentages by weight unless otherwise specified.

EXAMPLE I

In a 300 milliliter, 1-necked round bottom flask equipped with a magnetic stirring bar, 5.9 grams of L-proline was suspended in about 40 milliliters of acetonitrile until a dry nitrogen atmosphere. The suspension was cooled and 12.2 grams of 1,1,3,3-tertramethylguanidine was added dropwise while maintaining the temperature of the reaction mixture at from 0° C. to 10° C. Upon completion of the addition a solution resulted. Over a period of 10 minutes a solution of 12.5 grams of 1-(tertiary-butoxycarbonyl)imidazole in 10 milliliters of acetonitrile was added. The resulting slightly yellowish solution was then stirred overnight at room temperature. The reaction mixture was then cooled to less than 10° C. and 60 milliliters of crushed ice in 60 milliliters of water was added. The solution was washed with 40 milliliters of fresh ethyl acetate three times. After the final phase separation, the alkaline aqueous phase was acidified with about 60 milliliters of 3 molar aqueous potassium hydrogen sulfate to pH 2.5 from an initial pH of 13.0. A white suspension formed as the pH dropped below 7. The suspension was extracted with 50 milliliters of fresh ethyl acetate eight times. The eight ethyl acetate extracts were combined and washed with 50 milliliters of fresh water four times and with 50 milliliters of fresh saturated aqueous sodium chloride solution three times. After the final phase separation the organic phase was dried over anhydrous sodium sulfate and then filtered to remove the solids. Solvent was then removed from the organic liquid filtrate in a rotary evaporator under vacuum to produce 9.7 grams of white solid. The white solid was suspended in about 50 milliliters of petroleum ether for one hour, filtered, washed with petroleum ether, and dried to produce about 9.0 grams of solid product which melted in the range of 131° C. to 134° C. The product was N-(tertiary-butoxycarbonyl)-L-proline of about 97 percent purity. The yeidl of N-(tertiary-butoxycarbonyl)-L-proline based on L-proline was about 79 percent.

EXAMPLE II

In a 250 milliliter, 1-necked round bottom flask equipped as in Example I, 3.0 grams of L-proline was suspended in 20 milliliters of acetonitrile under a dry nitrogen atmosphere. The suspension was cooled below 10° C. and 6.0 grams of 1,1,3,3-tetramethylguanidine was added dropwise. The resulting yellow solution was stirred rapidly while 0.5 gram of 4-(dimethylamino)-pyridine was added and while a solution of 6.6 grams of 1-(tertiary-butoxy-carbonyl)imidazole in 20 milliliters of acetonitrile was added over a period of about 5 minutes with the temperature of the reaction mixture being maintained at 0° C. to 5° C. The yellow solution was then stirred at room temperature for 40 hours. The reaction mixture was cooled to 0° C. to 5° C. and 50 milliliters of crushed ice in 50 milliliters of water was added. The alkaline solution was washed with 40 milliliters of fresh ethyl acetate three times. After the final phase separation, the alkaline aqueous phase was acidified with about 25 milliliters of 3 molar aqueous potassium hydrogen sulfate to pH 2.50 at 0° C. to 5° C. The pH profile during acidification was:

| 3M KHSO$_4$ Added, milliliters, cumulative | pH |
| --- | --- |
| 0 | 11.07 |
| 1 | 8.50 |
| 4 | 7.50 |
| 8 | 6.70 |
| 10 | 5.30 |
| 12 | 5.00 |

| 3M KHSO$_4$ Added, milliliters, cumulative | pH |
| --- | --- |
| 15 | 4.50 |
| 20 | 3.75 |
| 25 | 2.50 |

The acidic solution was extracted with 40 milliliters of fresh ethyl acetate nine times. The nine ethyl acetate extracts were combined and washed with 40 milliliters of fresh water three times and with 40 milliliters of fresh saturated aqueous sodium chloride solution five times. After the final phase separation the organic phase was dried over anhydrous sodium sulfate and then filtered to remove the solids. Solvent was then removed from the organic liquid filtrate in a rotary evaporator under vacuum to produce 5.2 grams of product which was a white powder. High performance liquid chromatography showed the product to contain 91.6 area percent N-(tertiary-butoxycarbonyl)-L-proline, 4.8 area percent imidazole, and 0.99 area percent L-proline. The yield of N-(tertiarybutoxycarbonyl)-L-proline based on L-proline was about 85 percent.

EXAMPLE III

In a 250 milliliter, 1-necked round bottom flask equipped as in Example I, 3.5 grams of L-proline was suspended in 40 milliliters of acetonitrile under a dry nitrogen atmosphere. The suspension was cooled below 10° C. and 4.2 grams of 1,1,3,3-tetramethylguanidine, 3.2 grams of triethylamine, and 1.0 gram of 4-(dimethylamino)pyridine were added squentially. To the rapidly stirred suspension, 7.7 grams of 1-(tertiary-butoxycarbonyl)imidazole in 10 milliliters of acetonitrile was added. The reaction mixture was stirred for 24 hours at room temperature. During this stirring period the reaction mixture turned to a clear solution. The reaction mixture was cooled to 0° C. to 5° C. and 50 milliliters of crushed ice in 50 milliliters of water was added. The solution was washed with 40 milliliters of fresh ethyl acetate three times. After the final phase separation the alkaline aqueous phase was acidified with 21 milliliters of 3 molar aqueous potassium hydrogen sulfate to pH 2.40 at 0° C. to 5° C. The pH profile during acidification was:

| 3M KHSO$_4$ Added, milliliters, cumulative | pH |
| --- | --- |
| 0 | 11.47 |
| 1.5 | 8.66 |
| 3.0 | 7.95 |
| 6.0 | 7.10 |
| 10.0 | 5.02 |
| 15.0 | 4.10 |
| 20.0 | 2.79 |
| 21.0 | 2.40 |

The acidified reaction mixture was extracted with 40 milliliters of fresh ethyl acetate nine times. The nine ethyl acetate extracts were combined and washed with 40 milliliters of fresh water three times and with 40 milliliters of fresh saturated aqueous sodium chloride solution five times. After the final phase separation the organic phase was dried over anhydrous sodium sulfate and then filtered to remove the solids. Solvent was then removed from the organic liquid filtrate in a rotary evaporator under vacuum to produce 6.0 grams of product which was an off-white solid. High performance liquid chromatography showed the product to contain 98.1 area percent N-(tertiary-butoxycarbonyl)-L-proline, 0.6 area percent L-proline, and 0.4 area percent imidazole. The yield of N-(tertiary-butoxycarbonyl)-L-proline based on L-proline was about 90 percent.

EXAMPLE IV

In a 250 milliliter, 1-necked round bottom flask equipped as in Example I, 3.8 grams of glycine was suspended in 40 milliliters of acetonitrile under a dry nitrogen atmosphere. The suspension was cooled below 10° C. and 12.3 grams of 1,1,3,3-tetramethylguanidine was added dropwise. To the rapidly stirred suspension, 12.7 grams of 1-(tertiary-butoxycarbonyl)imidazole in 10 milliliters of acetonitrile was added. The reaction mixture was stirred for 24 hours at room temperature. During the stirring period the reaction mixture turned to a clear solution. The reaction mixture was cooled below 10° C. and 60 milliliters of crushed ice in 60 milliliters of water was added. The solution was washed with 40 milliliters of fresh ethyl acetate four times. After the final phase separation the alkaline aqueous phase was acidified with about 55 milliliters of 3 molar aqueous potassium hydrogen sulfate to pH 2.50 from an initial pH of 13.10. The acidified reaction mixture was extracted with 50 milliliters of fresh ethyl acetate eight times. The eight ethyl acetate extracts were combined and washed with 40 milliliters of fresh water five times and with 40 milliliters of fresh saturated aqueous sodium chloride solution three times. After the final phase separation the organic phase was dried over anhydrous sodium sulfate and then filtered to remove the solids. Solvent was then removed from the organic liquid filtrate in a rotary evaporator under vacuum to produce 8.6 grams intermediate product which was a white solid. A thin layer chromatographic comparison of the intermediate product with an N-(tertiary-butoxycarbonyl)glycine standard confirmed that the intermediate product was N-(tertiary-butoxycarbonyl)glycine of rather high purity. The yield of the intermediate product based on glycine was about 97 percent. The intermediate product was recrystallized using 25 milliliters of ethyl acetate and 100 milliliters of petroleum ether and dried to produce 6.0 grams of solid final product in the form of needle-like crystals. The final product melted in the range of 87° C. to 88° C. A thin layer chromatographic comparison of the final product with an N-(tertiary-butoxycarbonyl)glycine standard confirmed that the final product was N-(tertiary-butoxycarbonyl)glycine of high purity. The yield of the final product based on glycine was about 67 percent. Sampling and recrystallization losses are believed to have had a significant adverse affect on the yield of the final product.

EXAMPLE V

In a 250 milliliters, 1-necked round bottom flask equipped with a magnetic stirring bar, 4.5 grams of L-alanine was suspended in about 50 milliliters of N,N-dimethylformamide under a dry nitrogen atmosphere. The suspension was cooled below 10° C. and 17.5 grams of 1,8-diazabicyclo[5.4.0]undec-7-ene was added dropwise. To the rapidly stirred suspension, 12.2 grams of 1-(tertiary-butoxycarbonyl)imidazole in 10 milliliters of N,N-dimethylformamide was added at room temperature. This was washed in with two 5 milliliter portions of N,N-dimethylformamide. The reaction mixture was stirred at room temperature over a weekend. During stirring period the reaction mixture turned to a clear solution. The reaction mixture was cooled to about 10° C. to about 15° C. and 60 milliliters of crushed ice in 60 milliliters of water was added. The solution was added with 40 milliliters of fresh ethyl acetate four times. After the final phase separation, the alkaline aqueous phase was acidified with about 90 milliliters of 3 molar aqueous potassium hydrogen sulfate to pH 2.50 from an initial pH of 12.60. The acidified reaction mixture was extracted with 40 milliliters of fresh ethyl acetate ten times. The ten ethyl acetate extracts were combined an washed with 40 milliliters of fresh water five times and with 40 milliliters of fresh saturated aqueous sodium chloride solution three times. After the final phase separation the organic phase was dried over anhydrous sodium sulfate and then filtered to remove the solids. Solvent was then removed from the organic liquid filtrate in a rotary evaporator under vacuum to produce a viscous oil. Petroleum ether was added and the mixture was seeded with N-(tertiary-butoxycarbonyl)-L-alanine to induce precipitation of a white solid. The mixture was filtered and the weight of the white solid was determined to be about 10 grams. The white solid was transferred to a flask, stirred with fresh petroleum ether for 1 hour, filtered, and dried to produce 8.5 grams of product which melted in the range of 79° C. to 83° C. High performance liquid chromatography showed the product to contain 98.7 area percent N-(tertiary-butoxycarbonyl)-L-alanine and about 1.3 percent of 1-(tertiary-butoxycarbonyl)imidazole and imidazole taken collectively. The yield of the product based on L-alanine was about 88 percent.

EXAMPLE VI

In a 250 milliliter, 1-necked round bottom flask equipped with a magnetic stirring bar, 4.5 grams of L-alanine was suspended in about 50 milliliters of N,N-dimethylformamide under a dry nitrogen atmosphere. The suspension was cooled to about 10° C. and 12.7 grams of 1,1,3,3-tetramethylguanidine was added dropwise. The suspension was then stirred at room temperature for about 90 minutes. To the rapidly stirred suspension, 12.2 grams of 1-(tertiary-butoxycarbonyl)imidazole in 10 milliliters of N,N-dimethylformamide was added. This was washed in with two 5 milliliter portions of N,N-dimethylformamide. The reaction mixture was stirred at room temperature for 48 hours. The reaction mixture was then cooled and 60 milliliters of crushed ice in 60 milliliters of water was added. The solution was washed with 40 milliliters of fresh ethyl acetate four times. After the final phase separation the alkaline aqueous phase was acidified with about 90 milliliters of 3 molar aqueous potassium hydrogen sulfate to pH 2.70 from an initial pH of 12.57. The acidified reaction mixture was extracted with 40 milliliters of fresh ethyl acetate ten times. The ten ethyl acetate extracts were combined and washed with 50 milliliters of fresh water four times and with 50 milliliters of fresh saturated aqueous sodium chloride solution three times. After the final phase separation the organic phase was dried over anhydrous sodium sulfae and then filtered to remove the solids. Solvent was then removed from the organic liquid filtrate in a rotary evaporator under vacuum to produce 6.0 grams of very viscous oil. Upon standing at room temperature over a weekend, the oil crystallized. Petroleum ether was added and the mixture was filtered. The solids were washed with fresh petroleum ether, filtered, and dried to produce 4.7 grams of product which was a white solid melting in the range of 80° C. to 83° C. The product was N-(tertiary-butoxycarbonyl)-L-alanine of high purity. The yield of the product based on L-alanine was about 49 percent.

Although the present invention has been described with reference to specific details of certain embodiments thereof, it is not intended that such detail should be regarded as limitations upon the scope of the invention except insofar as they are included in the accompanying claims.

I claim:

1. In a process wherein precursory amino acid salt comprising an amino acid anion having at least one unblocked amino or imino group and further comprising at least one cation is reacted with 1-(tertiary-alkoxycarbonyl)imidazole to produce N-(tertiary-alkoxycarbonyl)-blocked amino acid salt in which the tertiary-alkoxycarbonyl group is tertiary-butoxycarbonyl or tertiary-amyloxycarbonyl, the improvement wherein said cation contains a nitrogen cationic atom and the reaction is conducted in the liquid phase and in the presence of essentially inert organic solvent having a dielectric constant at 25° C. of at least about 4.

2. The process of claim 1 wherein said essentially inert organic solvent has a dielectric constant at 25° C. of at least about 10.

3. The process of claim 1 wherein said essentially inert organic solvent has a dielectric constant at 25° C. of at least about 25.

4. The process of claim 1 wherein said essentially inert organic solvent has a dielectric constant at 25° C. of at least about 35.

5. The process of claim 1 wherein the weight ratio of said essentially inert organic solvent to said precursory amino acid salt initially present is at least about 1:1.

6. The process of claim 1 wherein the water content of the reaction mixture during said reaction is less than about 1 percent by weight.

7. The process of claim 1 wherein the water content of the reaction mixture during said reaction is less than about 0.1 percent by weight.

8. The process of claim 1 wherein said reaction is conducted under substantially anhydrous conditions.

9. The process of claim 1 wherein said nitrogen cationic atom is directly bonded to at least one carbon atom.

10. The process of claim 1 wherein said tertiary-alkoxycarbonyl group is tertiary-butoxycarbonyl.

11. A process comprising:
   (a) reacting amino acid having at least one unblocked amino or imino group, which amino acid is dissolved or suspended in essentially inert organic solvent having a dielectric constant at 25° C. of at least about 4, with nitrogenous base to form a solution or suspension of precursory amino acid salt comprising an amino acid anion having at least one unblocked amino or imino group and further comprising at least one cation containing a nitrogen cationic atom; and
   (b) reacting, in the liquid phase and in the presence of essentially inert organic solvent having a dielectric constant of at least about 4, at least a portion of said precursory amino acid salt and 1-(tertiary-alkoxycarbonyl)-imidazole to produce N-(tertiary-alkoxycarbonyl)-blocked amino acid salt, wherein the tertiary-alkoxycarbonyl group is tertiary-butoxycarbonyl or tertiary-amyloxycarbonyl.

12. The process of claim 11 wherein the essentially inert organic solvent present in both reactions has a dielectric constant at 25° C. of at least about 10.

13. The process of claim 11 wherein the essentially inert organic solvent present in both reactions has a dielectric constant at 25° C. of at least about 25.

14. The process of claim 11 wherein the essentially inert organic solvent present in both reactions has a dielectric constant at 25° C. of at least about 35.

15. The process of claim 11 wherein the weight ratio of the essentially inert organic solvent to said amino acid having at least one unblocked amino or imino group initially present in the reaction of step (a) is at least about 3:1 and wherein the weight ratio of the essentially inert organic solvent to said precursory amino acid salt initially present in the reaction of step (b) is at least about 1:1.

16. The process of claim 11 wherein the water content of the reaction mixture during both reactions is less than about 1 percent by weight.

17. The process of claim 11 wherein the water content of the reaction mixtures during both reactions is less than about 0.1 percent by weight.

18. The process of claim 11 wherein the reaction of step (b) is conducted under substantially anhydrous conditions.

19. The process of claim 11 wherein both reactions are conducted under substantially anhydrous conditions.

20. The process of claim 11 wherein said nitrogen cationic atom is directly bonded to at least one carbon atom.

21. The process of claim 11 wherein said nitrogenous base has a pKa in water of greater than 7.

22. The process of claim 11 wherein said nitrogenous base has a pKa in water of at least about 8.

23. The process of claim 11 wherein said nitrogenous base has a pKa in water of at least about 10.

24. The process of claim 11 wherein said tertiary-alkoxycarbonyl group is tertiary-butoxycarbonyl.

* * * * *